United States Patent
Sartorius et al.

(10) Patent No.: US 9,354,168 B2
(45) Date of Patent: May 31, 2016

(54) METHOD AND APPARATUS FOR DETERMINING A SUBSTANCE USING THZ RADIATION

(75) Inventors: Bernd Sartorius, Berlin (DE); Helmut Roehle, Berlin (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 276 days.

(21) Appl. No.: 14/240,690

(22) PCT Filed: Jul. 31, 2012

(86) PCT No.: PCT/EP2012/003401
§ 371 (c)(1),
(2), (4) Date: Jun. 12, 2014

(87) PCT Pub. No.: WO2013/029746
PCT Pub. Date: Mar. 7, 2013

(65) Prior Publication Data
US 2014/0319356 A1   Oct. 30, 2014

(30) Foreign Application Priority Data

Aug. 31, 2011  (DE) .......................... 10 2011 112 697

(51) Int. Cl.
*G01N 21/35* (2014.01)
*G01N 21/55* (2014.01)
*G01N 21/3577* (2014.01)
(Continued)

(52) U.S. Cl.
CPC ............ *G01N 21/55* (2013.01); *G01N 21/3504* (2013.01); *G01N 21/3577* (2013.01); *G01N21/3586* (2013.01); *G01N 21/4133* (2013.01); *G01N 21/90* (2013.01); *G01N 21/9027* (2013.01); *G01N 2021/4153* (2013.01)
(Continued)

(58) Field of Classification Search
CPC .......... G01N 21/3504; G01N 21/9027; G01N 2021/4153
See application file for complete search history.

(56) References Cited

U.S. PATENT DOCUMENTS

| 5,864,395 A | 1/1999 | Laurberg |
| 2010/0292936 A1 | 11/2010 | Jepsen |

FOREIGN PATENT DOCUMENTS

| DE | 102009021843 | 12/2010 |
| DE | 102009051692 | 4/2011 |
| WO | WO-01/06915 | 2/2001 |

OTHER PUBLICATIONS

"International Application No. PCT/EP2012/003401, International Search Report and Written Opinion mailed Oct. 25, 2012", 18 pgs.
(Continued)

*Primary Examiner* — Casey Bryant
(74) *Attorney, Agent, or Firm* — Schwegman, Lundberg & Woessner, P.A.

(57) ABSTRACT

The invention relates to a method for determining a liquid in a closed container using THz radiation, in which a first and a second measurement are carried out, wherein the THz radiation is emitted in the direction of the liquid for measuring properties of the liquid, and a portion of the THz radiation coming from the direction of the liquid is detected. In the proposed method, the closed container contains, in addition to the liquid, a gas, wherein a wall of the container is transmissive for THz radiation and wherein the detected portion of the THz radiation in the first measurement is reflected at a boundary surface between the wall and the gas or a pocket containing the gas, and the second measurement is reflected at a boundary surface between the wall and the liquid. The first measurement thus serves as a reference measurement for capturing disturbing losses in the THz beam path and for determining influences of the wall on a measurement result for the second measurement. The invention further relates to an arrangement suitable for carrying out this method.

18 Claims, 2 Drawing Sheets

Figure 1:
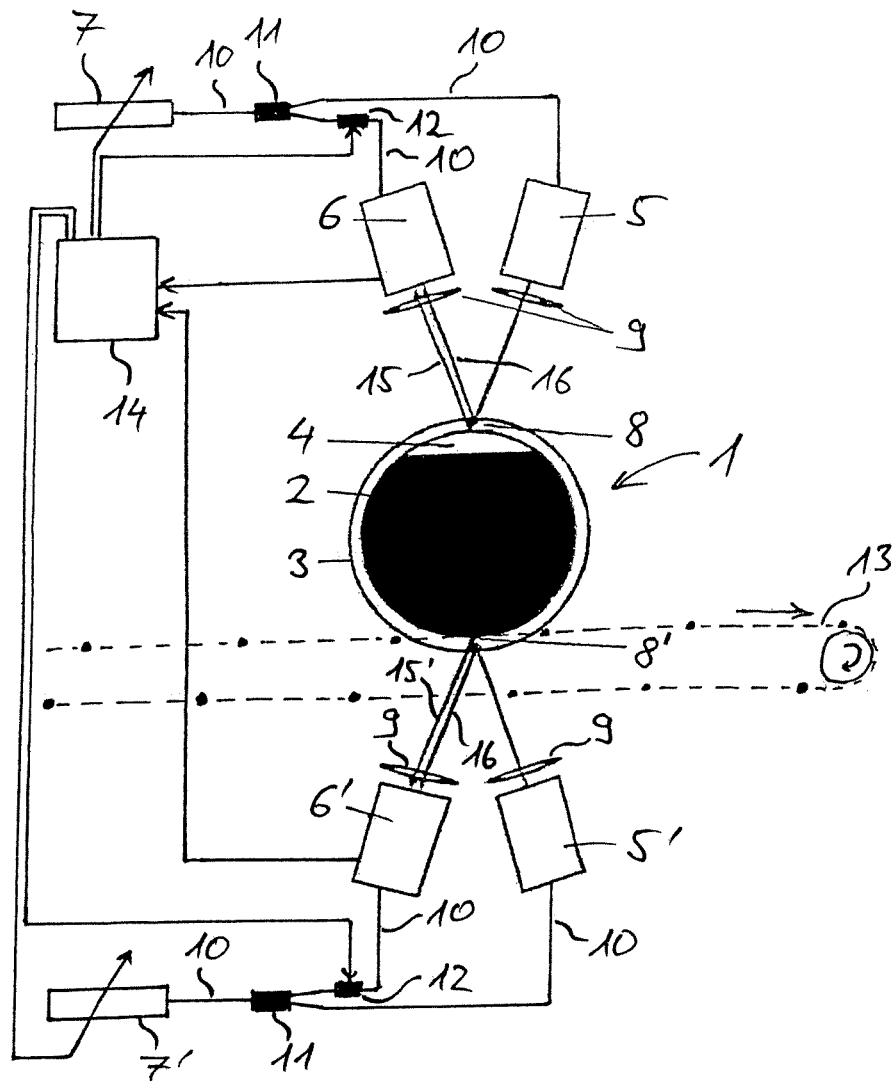

(51) Int. Cl.
*G01N 21/41* (2006.01)
*G01N 21/90* (2006.01)
*G01N 21/3586* (2014.01)
*G01N 21/3504* (2014.01)

(56) References Cited

OTHER PUBLICATIONS

Krumbholz, N., et al., "Handheld Terahertz Spectrometer for the Detection of Liquid Explosives", Millimetre Wave and Terahertz Sensors and Technology II, edited by Keith A. Krapels, Neil A. Salmon, Proc. of SPIE vol. 7485, 748504, (Sep. 17, 2009), 12 pgs.

Von Chrzanowski, Lars S, et al., "Capability of Terahertz-Wave Instrumentation for Non Destructive Testing of Liquids", 10th European Conference on Non-Destructive Testing, XP002685244, Moscow [http://www.ndt.net/article/ecndt2010/reports/1_05_16.pdf], (Jun. 7, 2010), 8 pgs.

"International Application No. PCT/EP2012/003401, International Preliminary Report on Patentability (English) mailed Mar. 13, 2014", 13 pgs.

METHOD AND APPARATUS FOR DETERMINING A SUBSTANCE USING THZ RADIATION

PRIORITY CLAIM TO RELATED APPLICATIONS

This application is a national stage application under 35 U.S.C. §371 of PCT/EP2012/003401, filed Jul. 31, 2012, and published as WO 2013/029746 on Mar. 7, 2013, which claims priority to German Application No. 10 2011 112 697.3, filed Aug. 31, 2011, which applications and publication are incorporated by reference as if reproduced herein and made a part hereof in their entirety, and the benefit of priority of each of which is claimed herein.

The invention relates to a method for determining a substance amid the use of THz radiation, according to the preamble of the main claim, as well as to an arrangement which is suitable for carrying out such a method.

With a method of the known type, a first and a second measurement are carried out, wherein the THz radiation is emitted in the direction of the substance and a share of the THz radiation coming from the direction of the substance is detected, for measuring characteristics of the substance. Such a method is known for example from the document DE 10 2009 051 692 B3.

Materials which are at least partly transparent to the THz radiation can be analysed with the known methods. An unsolved problem however is the analysis of liquids—in particular aqueous liquids which as a rule are opaque to THz radiation—and which are located in a closed container which itself is manufactured of a firstly unknown material. This problem can e.g. arise in the context security checks at airports. Thereby, in particular dangerous substances should be able to be differentiated from harmless drinks, without the container containing the liquid—typically a bottle or likewise—having to be opened for this. Known means such as snooping portals or X-ray apparatus do not solve this problem.

It is therefore the object of the invention, to determine a liquid located in a closed container, at least so accurately that it can be assigned to a class of liquids or be differentiated from a certain different liquid or class of liquids, and specifically such that the container does not need to be opened for this.

According to the invention, this object is achieved by a method with the characterising features of the main claim in combination with the features of the preamble of the main claim, as well as by an arrangement with the features of the auxiliary claim which is suitable for carrying out this method.

With the suggested method, the substance to be determined in thus a liquid which is located in a closed container additionally containing a gas, wherein a wall of the container is transparent to THz radiation. Here too, two measurements are carried out amid the use of THz radiation, wherein in each case for measuring characteristics of the liquid, the THz radiation is emitted in the direction of the liquid and a share of the THz radiation coming from the direction of the liquid is detected. Thereby, the detected share of the THz radiation with the first measurement is reflected at a boundary surface between the wall and the gas or a bubble containing the gas, and with the second measurement at a boundary surface between the wall and the liquid, wherein the first measurement serves as a reference measurement for determining influences of the wall and/or of the THz beam path on the measurement result of the second measurement.

The method can be carried out in a simple manner, by way of the THz radiation, with the first measurement, being directed for this onto a location of the wall, at which the gas or the bubble containing the gas contacts the wall, whereas the THz radiation with the second measurement is directed onto a location of the wall, at which the liquid contacts the wall. For this, the container, e.g. with the first measurement, can be beamed from above in the region of the gas bubble, and with a second measurement from below in the region filled with liquid. Thereby, it is insignificant as to whether the reference measurement indicated here as the first measurement, is carried out before or after the second measurement or simultaneously with this.

THz radiation is to be indicated in particular as electromagnetic radiation with frequencies of between 0.05 THz and 10 THz. The frequency is typically between 0.05 THz and 2 THz.

The container with the liquid, for example a bottle, is closed and can advantageously also remain closed with the suggested method.

The invention is based on the insight that an intensity of the share of the THz radiation which is detected after a reflection at the boundary surface between the wall and the liquid—thus with the second measurement—not only depends on the characteristics of the liquid, but also on characteristics of the wall, in particular on a refractive index of a material forming the wall. Moreover, disturbing influences on the path of the THz radiation from an applied terahertz emitter to the reflecting location and from there to an applied terahertz receiver are taken into account. These are intensity losses, e.g. by absorption in the wall of the container, by way of rough surface structures of the wall, be way of stuck-on labels or by way of dirt. The refractive index of the liquid can be determined if the disturbing influences are eliminated and if the degree of reflection—thus a ratio of an intensity of incident radiation and of the intensity of the reflected radiation—at the boundary surface between the wall and liquid as well as the refractive index of the material forming the wall are known. Disturbing influences can be minimised by way of suitable constructions with laboratory measurement, and a refractive index of cuvettes which are thereby applied is known. It is a problem when, despite disturbing influences on the path of the THz radiation and with an unknown refractive index of a wall material of the container, the liquid located therein is to be determined. This problem is now solved by way of the reference measurement being additionally carried out.

With the help of the reference measurement, firstly the disturbing effects—thus the intensity losses—in the THz beam path can be very comprehensively detected and a reference value taking these into account can be produced. Moreover, one can make use of the fact that the reflection degree with the reflection at the boundary surface between the wall and the gas depends less on an unknown than with the reflection at the boundary surface between the wall and the liquid, since to a very good approximation, one can assume that the gas has a refractive index of 1. Details on the refractive index of the material forming the wall of the container can also be obtained and/or a measure of the absorption characteristics of the wall can be determined by way of this. Even if this material is not known beforehand, a refractive index of the liquid can then at least be roughly determined by way of the second measurement therefore being evaluated in a manner depending on a result of the first measurement. Thus the liquid in turn can be determined or at least assigned to a class.

In order to ensure that the influences of the THz beam path and of the wall are identical with both measurements, one can envisage the location of the wall, onto which the THz radiation is directed with the second measurement, being identical to the location of the wall, onto which the THz radiation is directed with the first measurement. For this, the container can be moved such that with the first measurement, it is the gas or the bubble and with the second measurement it is the liquid which contacts the wall at this location. This can be effected by way of the container being fixed relative to an applied measurement system with a THz emitter and THz receiver and being rotated or tilted together with the latter.

The measurement with an absolutely identical THz beam path with the unchanged equally disturbing losses at a measurement point which is identical for both measurements, only changes its contact with the gas or the gas bubble with the one measurement and with the fluid with the other measurement and in many respects represents the best method for realising the reference measurement and the liquid measurement.

This perfect reference formation even functions if the container is located in a further packaging, i.e. in a travel bag or cardboard box, as long as the complete arrangement remains fixed to one another and is tilted or rotated in its entirety. Only the contact of the inner surface of the container to either the gas or the liquid then changes in its entirety, and only this change is detected in the difference formation or ratio formation of reference signal to measurement signal.

The disadvantage with the described implementation of both measurements at the same location is merely the effort for the mechanical fixation and movement and the course of measurement which is slowed due to the necessary movement.

As an alternative, i.e. for very rapid measurements, it is therefore also conceivable, instead of carrying out a movement of the container between the measurements, to carry out the two measurements at different locations of the wall. In particular, in this case, the container for the first and the second measurement can be positioned in a lying manner and/or in a manner such that the gas collects in a region of the container, in which a vertical cross section of the wall of the container is circular and/or a displays a constant wall thickness. Thus one can avoid a result of the method being adulterated by influences of the wall on both measurements, said influences differing too much due to different wall characteristics.

Preferably, a beam intensity measured with the first measurement is applied as a reference value, and the refractive index of the liquid is determined in a manner depending on the ratio of a beam intensity measured with the second measurement and this reference value. Moreover, the refractive index of the material forming the wall can be determined with the first measurement and/or the second measurement, which is typically effected in an indirect manner, wherein the refractive index of the liquid is then determined by way of a result of the second measurement being evaluated in dependence on the thus determined refractive index of the material forming the wall.

For this, a numeric relation between the power $P_e$ of the radiation incident on the boundary surface between the wall and the liquid, the power $P_r$ of the radiation reflected there, the refractive index $N_1$ of the material forming the wall and the refractive index $N_2$ of the liquid can be evaluated. This relationship results from the Fresnel formulae and assumes the form: $P_r = P_e (|N_2 - N_1|/|N_2 + N_1|)^2$ e.g. for the specific case of a negligible angle of incidence and angle of reflection and amid the realistic assumption of an equal magnetic permeability of the wall and liquid. With the evaluation, one can take into account the fact that for the power $P_r'$ of the radiation reflected at the boundary surface between the wall and the gas with the reference measurements, amid the same assumptions, to a large accuracy $Pr' = P_e(|1 - N_1|/|1 + N_1|)^2$ and that the ratio $P_r/Pr'$ corresponds to the ratio of the powers or intensities which are detected with the two measurements. Specifically, it can be assumed that the refractive index of the gas in the container is at least approximately has the value 1.

It is helpful if with the first measurement and/or with the second measurement, additionally to the mentioned share, a beam intensity reflected at an outer surface of the container is detected and a travel time (transit time or propagation time) difference and/or an intensity difference between the share reflected at the respective boundary surface between the wall and the gas or the liquid, and the beam share reflected at the outer surface are determined. Then, an optical thickness of the wall can be determined from the travel time difference, and a measure for an absorption behaviour of a material forming the wall, e.g. an absorption coefficient can be determined from the intensity difference. With this, with almost certainty, one can deduce the material of the wall or assign this material at least to a class, which permits one to conclude the refractive index of the wall material. A data bank can e.g. be evaluated for this, or a stored table can be read out.

One can envisage the first and/or the second measurement being carried out in each case several times at different locations of the wall and/or at difference frequencies of the THz radiation. A statistic error of the method can be reduced by way of carrying out both measurements at different locations. An implementation of at least one of the measurements at different frequencies firstly simplifies the determining of the wall material, by way of a frequency dependency of the absorption in the wall material being determined, so that the refractive index of the liquid can also be determined more accurately. If the second measurement is also carried out at different frequencies, then again one obtains values for the refractive index of the liquid at different frequencies, by which means the liquid can be determined more accurately. Thereby, e.g. a frequency region of 0.1 THz to 0.5 THz or 1 THz, even better from 0.05 THz to 2 THz can be sampled with these measurements.

A method with which firstly the second measurement is carried out on the inner surface of the wall which is covered with liquid, the container is then rotated or tilted, in order to bring the inner surface of the wall at the fixed measurement point into the region of the gas or the gas bubble and a measurement series in a defined temporal sequence is then carried out, is also advantageous. The speed of the wetting change can e.g. be determined by an evaluation unit of the applied arrangement. Liquids can differ significantly from one another with regard to this characteristic. In particular, water displays significantly different wetting characteristics than most other liquids. Thus a further parameter can be deduced for recognising the liquid.

If the evaluation of the first and second measurement, which e.g. can be effected by way of a difference formation or ratio formation, with the relative arrangement of the terahertz emitter and terahertz receiver to the container and which is described further above and is the same in each case during these two measurements, is combined with a measurement—thus with an implementation of the first as well as the second measurement—at several locations and with a picture formation, then the existence of a container with a liquid can be recognised in a package. If the change of the measurement signal given a rotation or tilting in this case, as described in the previous paragraph, is again examined in a time-resolved manner, then liquids with a slower wetting change—in particular e.g. water—can be differentiated from those with rapid wetting changes. With rapid movements bottles with—non-hazardous—water-containing drinks, on account of the low wetting change, only lead to very small signal change between the reference measurement, with which, although per se the gas contacts the wall, the wall however is still wetted with a liquid film, and the actual liquid measurement. With other, potentially dangerous liquids with a rapid wetting change—e.g. petrol—in contrast a clear change of the signal is to be ascertained even with rapid rotation or tilting movements. Thus one can differentiate non-hazardous water and water-containing drinks from potentially dangerous petrol and related liquids by way of the different behaviour of the difference signal with rapid rotation or tilting movements, and specifically also in closed containers which for their part are packaged and are located for example in travel bags or cardboard boxes.

The method can be carried out with a phase-sensitive THz system with at least one optically activatable THz emitter antenna and with at least one optically activatable THz receiver antenna for the coherent detection of the THz radiation produced by the THz emitter antenna, with which the THz remitter antenna and the THz receiver antenna are activated by a common light source, in order to permit an evaluation of the optical thickness of the wall. With regard to the light source, it is thereby the case of a pulsed laser for producing pulses with frequency components in the THz region, or of a continuous laser light source which produces an optical beat signal in the THz region. A suitable THz system of this type is e.g. described in the document WO 01/06915 A1.

Thereby, it is possible for the first and the second measurement to use the same THz emitter antenna and THz receiver antenna or for each of the two measurements to envisage their own THz emitter antenna and THz receiver antenna in each case. In any case, it is advantageous if not only amplitude or intensity of the respective reflected share of the THz radiation is measured, but also a phase, which is possible with THz systems of the described type. Thus the complex refractive index can be determined in each case.

What is put forward is also an arrangement for determining a liquid located in a closed container, and which is suitable for carrying out the described method. This arrangement comprises at least one terahertz emitter for producing THz radiation, at least one terahertz receiver for detecting THz radiation as well as an evaluation unit which is connected to the at least one terahertz receiver and is for evaluating output signals of the terahertz receiver, wherein the terahertz emitter and the terahertz receiver are arranged relative to one another such that the terahertz receiver is suitable for detecting the THz radiation produced by the terahertz emitter, after a reflection at a defined location of an inner surface of a wall of the container. The evaluation unit of the suggested arrangement with regard to programming technology is configured to evaluate the output signals for a first measurement and a second measurement and thereby to derive a reference value for an intensity of the detected THz radiation from the output signals for the first measurement and to evaluate the output signals for the second measurement in dependence on the reference value and by way of this to derive a refractive index of the liquid located in the container and/or to assign the liquid to a liquid class.

Thereby, the configuration of the evaluation unit with regard to programming technology is based on the assumption, that the THz radiation with the first measurement is reflected at a location, at which a gas or gas bubble contained in the container additionally to the liquid contacts the wall of the container, and with the second measurement is reflected at a location, at which the liquid contacts the wall of the container, which corresponds to a correct application of the arrangement.

The evaluation unit can moreover be configured to derive in each case an intensity of a share of the THz radiation reflected at the outer surface of the wall of the container and an intensity of a share of the THz radiation which is reflected at the inner surface of the wall of the container, as well as a travel time difference between these two shares, from the output signals. The terahertz receiver should be synchronised with the terahertz emitter in order to permit this. This may be realised without any problem if the terahertz emitter comprises an optically activatable THz emitter antenna, and the terahertz receiver an optically activatable THz receiver antenna for the coherent detection of the THz radiation produced by the THz emitter antenna and if a common light source is provided for activating the THz emitter antenna as well as the THz receiver antenna.

Then the evaluation unit can also be configured to derive an optical thickness of the wall of the container from the travel time difference, to derive a measure for an absorption behaviour of the wall material from the mentioned intensities in dependence on the optical thickness, to identify the wall material in dependence on this measure and possibly additionally depending on the determined thickness, as corresponding to a certain substance or as belonging to a certain substance class, e.g. by way of comparison to typical values or thresholds, which e.g. can be stored in a data bank or be deposited in the evaluation unit, to determine the refractive index of the wall material as corresponding to a value which is stored for this substance or this substance class in a memory, which in turn can be contained in the evaluation unit or be given by an external data bank.

The evaluation unit can moreover be configured to determine the refractive index of the liquid by way of evaluating a result of the second measurement in dependence on the thus determined refractive index of the wall material.

This functions best if a frequency dependency of the absorption behaviour of the wall material is determined, thus if the mentioned measure is determined for different frequencies. For this, the evaluation unit can comprise a device for activating the terahertz emitter, said device being configured to activate the terahertz emitter such that it produces the THz radiation successively or simultaneously at different frequencies, wherein the evaluation unit is configured, by way of evaluating the output signals at the respective frequency, to carry out at least one of the two measurements for each of these frequencies.

One can envisage the arrangement also comprising a holding device for the container, the terahertz emitter and the terahertz receiver, by way of which the container, terahertz emitter and the terahertz receiver are fixed relative to one another during the measurements, wherein the entirety however is also designed in such a rotatable or tiltable manner by way of the holding device, that the measurement point irradiated by the THz radiation is covered once by the gas bubble and once by the liquid. With this, the reference measurement and liquid measurement can be carried out at a single location of the wall, and also the disturbing losses in the THz beam path are identical and are fully taken into account with the reference measurement and are compensated with the evaluation.

However, it is also possible for the arrangement to comprise two pairs of in each case one terahertz emitter and one terahertz receiver, of which one is arranged higher than the other, wherein the pair which is arranged higher is provided for the first measurement at the gas bubble and the other, thus the lower pair is envisaged for the second measurement at the liquid.

Additionally, the arrangement can comprise a conveying device, in order for the two measurements, to automatically convey the container to a measurement location and/or to rotate it or pivot it at the measurement location, for example a conveyor belt or a displaceable, rotatable or pivotable holder for the container.

Finally, one can envisage the terahertz emitter and the terahertz receiver in each case comprising THz optics, in order to focus or image the produced THz radiation onto the respective location of the wall, and the THz radiation reflected there onto the THz receiver antenna.

Figure 2:
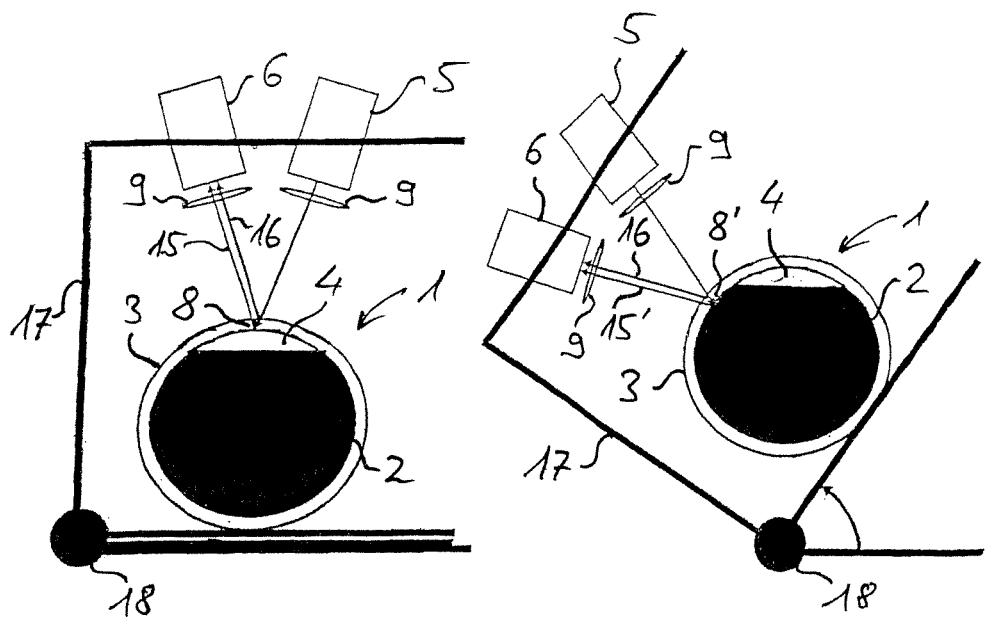

Embodiment examples of the invention are hereinafter explained by way of the FIGS. 1 to 3. There are shown in:

FIG. 1 a cross section through an arrangement for determining a liquid located in a bottle, amid the use of THz radiation, FIG. 2 cross sections through an arrangement serving the same purpose, in another embodiment, in two different conditions and FIG. 3 again in two different conditions, in each case a longitudinal section through a respective arrangement in an embodiment similar to the embodiment example from FIG. 2.

A container 1 which is represented in cross section can be recognised in FIG. 1, with which it is the case of a closed bottle and in which a liquid 2 is located. With regard to the liquid 2 it is the case of a liquid which is not known at first. Moreover, a priori, it also not known, from which material a wall 3 of the container is formed, which however is at least partly transparent to the THz radiation. A gas which forms a gas bubble in the upper part of the container 1 is located in the container 1 additionally to the liquid 2.

What is represented in FIG. 1 is also an arrangement for determining the liquid 2 located in the container 1. This arrangement comprises two terahertz emitters 5 and 5' each with an optically activatable THz emitter antenna as well as in each case a terahertz receiver 6 and 6' assigned to this terahertz emitter 5 and 5' respectively, for each of the terahertz emitters 5 and 5'. The terahertz receivers 6 and 6' each comprise an optically activatable THz receiver antenna.

The terahertz emitter 5 and the terahertz receiver 6 form a pair, to which a common light source 7 for activating the THz emitter antenna as well as the THz receiver antenna of the terahertz receiver 6 is assigned. In the same manner, a common light source 7', with which the THz emitter antenna of the terahertz emitter 5 as well as the THz receiver antenna of the terahertz receiver 6 is activated, is assigned to the terahertz emitter 5' and to the terahertz receiver 6'.

The terahertz emitter 5 and the terahertz receiver 6 are arranged relative to one another and to the container 1, such that a THz radiation reduced by the terahertz emitter 5, after a reflection at a defined location 8 of the wall in an upper region of the container, can be detected by the terahertz receiver 6. In a similar manner, the terahertz emitter 5' and the terahertz receiver 6' are arranged relative to one another and to the container 1 such that a THz radiation produced by the terahertz emitter 5' after a reflection at a defined location 8' of the wall in a lower region of the container 1 can be detected by the terahertz receiver 6'. For this, the terahertz emitters 5 and 5' as well as the terahertz receivers 6 and 6' each have THz optics 9.

With regard to the light sources 7 and 7', it is the case in each case of a pulsed laser whose light pulses are beamed in the fs-region onto light-sensitive elements of the respective THz emitter antenna and of the respective THz receiver antenna. The received THz pulse is sampled due to the relative delay of the pulses on their way to the emitter antenna or receiver antenna, and are converted by way of a subsequent Fourier transformation into a THz spectrum, for example over a region of 0.05 THz to 2 THz.

The light sources 7 are connected to the respective terahertz emitter 5 and 5' and to the respective terahertz receiver 6 and 6' via waveguides 10 and a beam splitter 11 in each case. Moreover, in each case an adjustable optical delay circuit 12 is connected between the beam splitters 11 and the respective terahertz receiver 6 and 6'. Thus the laser light source 7 with the terahertz emitter 5 and the terahertz receiver 6, as well as the laser light source 7' with the terahertz emitter 5' and the terahertz receiver 6' in each case form a phase-sensitive THz system which permits a coherent detection of the THz radiation produced by the respective THz emitter antenna. Thus not only can an intensity or power, but also a phase or travel time of the detected THz radiation be determined.

It is also possible for the light sources 7 and 7' not to be designed as pulsed lasers, but as continuous laser light sources which produce two light components of a slightly different wavelength which are superimposed with one another, so that a beat signal in the THz region arises, with which the THz antennae are activated. Such light sources are also called CW sources, wherein CW stands for continuous wave. Thereby, again the frequency of the lastly produced THz radiation can be adjusted over a desired interval for example 0.05 THz to 2 THz, by way of detuning in each case at least one of the wavelengths.

A conveyor belt 13, with which the container 1 can be automatically transported to a measurement location—here between the two THz systems—and held there, is shown schematically in FIG. 1. The container can also be led by the conveyor belt 13 past the measurement beam during the method, so that several measurement points along the bottle can be examined Thus via inhomogeneities, one can determine what increases the evaluation accuracy.

Finally, the arrangement of FIG. 1 comprises an evaluation unit 14. The evaluation unit 14 with regard to programming technology is configured to evaluate output signals of the terahertz receivers 6 and 6', and specifically for a first measurement, with which a share 15 of the THz radiation which is reflected at a boundary surface between the wall 3 and the gas 4 is detected, and for a second measurement, with which a share 15' of the THz radiation which is reflected at a boundary surface between the wall 3 and the liquid 2 is detected. The first measurement thereby serves as a reference measurement, with which disturbing influences in the THz beam path—i.e. intensity losses—are taken into account and influences of the wall 3 on the measurement result of the second measurement are determined. Moreover, with both measurements, a beam share 16 reflected at an outer surface of the container 1 is detected. In the present case, the THz system with the terahertz emitter 5 and the terahertz 6 is used for the first measurement, and the THz system with the terahertz emitter 5' and the terahertz receiver 6' is used for the second measurement.

The evaluation unit 14 comprises a device for activating the light sources 7 and 7' and thus the terahertz emitters 5 and 5'. The time position of the pulses or of the beat signals of the light sources 7 and 7' are adjusted with this device, such that the received THz radiation is temporally sampled and coherently detected. Moreover, a frequency tuning is effected with the beat signal by way of wavelength tuning of the laser. Thus the measurements can e.g. be carried out over the whole frequency range of 0.1 THz to 1 THz or from 0.05 THz to 2 THz.

The evaluation unit 14 is programmed such that in each case, an intensity of the beam share 16 reflected at the outer surface of the wall 3, an intensity of the share 15 and 15' of the THz radiation which is reflected at the boundary surface between the wall 3 and the gas 4 or the liquid 2 respectively— thus at the inner surface of the wall, and a travel time difference between these two beam shares 16 and 15 or 16 and 15' can be derived from the output signals. Thereby, in each case the optical delay circuits 12 which are activated for this by the evaluation unit 14 are adjusted with the measurements, and a dependency of the output signal on a setting of the delay circuit 12 is examined, for determining the travel time difference. The reflected THz radiation is thereby also detected with regard to its phase.

An optical thickness of the wall 3 is directly derived by the evaluation unit 14 from the travel time difference which will be the same with both measurements. By way of a difference between the intensity determined for the beam share 16 and the intensity determined for the share 15 being evaluated for the different frequencies of THz radiation amid the use of the optical thickness, the evaluation unit 14 determines a spectral course of absorption behaviour of the material forming the wall 3. The thus determined spectral course, which for each of the frequencies defines a measure for the absorption behaviour at this frequency and for example can express the absorption coefficient as a function of the frequency, is now compared to typical spectral courses or to thresholds for the different frequencies. The material of the wall 3 is indentified by way of this with the evaluation unit 14, at least as belonging to a certain substance class. The typical spectral courses or thresholds for this are stored in a memory in the evaluation unit 14. A refractive index as a function of the frequency is stored in the memory of the evaluation unit for every substance to be considered or for every substance class to be considered, so that simultaneously a refractive index of the material of the wall is determined by the evaluation unit 14 for each of the frequencies used with the measurements.

The evaluation unit 14 is moreover configured, by way of the evaluation of the output signals of the terahertz receiver 6 which are obtained with the first measurement, to determine a reference value for the intensity of the detected THz radiation, said reference value being used with the valuation of the second measurement. The output signals of the terahertz receiver 6' which are obtained with the second measurement are thus evaluated for each of the used frequencies, in each case in dependence on the refractive index determined for the material of the wall 3 and on the reference value. The reference value can be defined e.g. as a computed 100% signal, corresponding to an intensity value which would result with a 100% reflection at the boundary surface, corresponding to a reflection degree of 1.

Finally, by way of this, a refractive index of the liquid 2 located in the container 1 is derived for each of the applied frequencies, and specifically in a manner depending on a ratio of the intensity of the share 15' which is measured with the second measured and the reference value, wherein both can be normalised by the intensity determined for the beam share 16 in each case. Neglecting the very small angle of incidence and angle of reflection, the equation $$I'/I = [(|N_2 - N_1| \times |1 + N_1|)/(|N_2 + N_1| \times |1 - N_1|)]^2$$

can be solved for $N_2$ for determining the refractive index of the liquid 2 at a certain frequency. In this equation, I indicates the intensity which is measured with the first measurement for the share 15, and I' the intensity measured with the second measurement for the share 15'—preferably in each case normalised by the intensity measured for the beam share 16—as well as $N_1$ the refractive index of the material of the wall 3 which can be determined at least approximately in the previously described manner, and $N_2$ the refractive index of the liquid 2 which is finally to be determined. This relationship results directly from the citations with regard to the Fresnel formulae in the general description part.

At the latest, when the refractive index of the liquid 2 is determined for sufficiently as many different frequencies from the THz region, then from this, one can easily conclude the liquid 2 itself or the liquid 2 can at least be identified as belonging to a class of hazardous or non-hazardous substances or materials. This identification can be carried out automatically by the evaluation unit 14 by way of a suitable programming With the method for determining the liquid 2 which is described here and which is carried out with the arrangement of FIG. 1, the container 1 which remains closed during all measurements is arranged in a lying manner and as a consequence is positioned such that the gas 4 collects in a region of the container, in which a vertical cross section of the wall 3 which can be recognised in FIG. 1, is circular and has a constant wall thickness. It is thus ensured that the characteristic of the wall 3 at the location 8, at which the reference measurement is carried out, are comparable with its characteristics at the location 8, at which the second measurement is carried out. The two measurements thereby in the present embodiment example can be carried out simultaneously. Even if the container 1 is shaped differently, the locations 8 and 8' should be selected such that to all intents and purposes they are equivalent with regard to the wall thickness, surface nature and curvature characteristics.

The method becomes even more precise, if the two measurements in contrast are carried out one after the other, and the container 2 is moved between the two measurements such that the location 8 of the wall 3 with the first measurement is identical to the location 8' of the wall 3 with the second measurement. This e.g. can be achieved if the two measurement points lie exactly opposite one another and the container is rotated by 180° about its longitudinal axis between the two measurements. For this, a device for rotating the container 1 can be provided additionally to the conveyor belt 13.

Alternatively or additionally, it is also possible for both measurements to not only be carried out at different frequencies, but also in each case at several locations of the wall 3, in order to reduce statistical errors. For this, the container can e.g. be rotated by 360° about its longitudinal axis and thereby the first and the second measurement carried out repeatedly. Thus inhomgieneities of the bottle can be recognised and taken into account.

Figure 3:
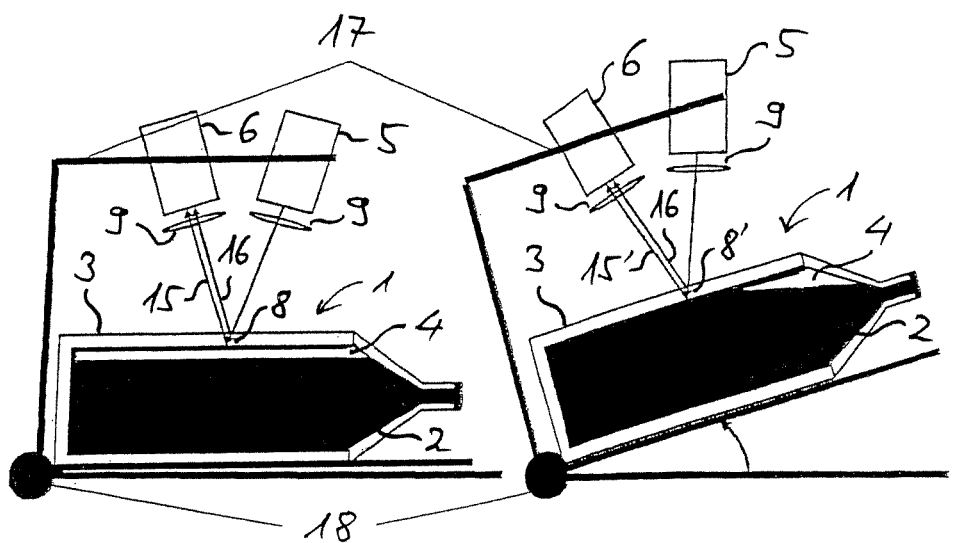

Two comparable arrangements are shown in the FIGS. 2 and 3. Recurring features here are again provided with the same reference numerals. What are not shown, but are provided in the same manner as with the previous embodiment example, are a light source for activating the terahertz emitter 5 and the terahertz receiver 6 and which as described previously is optically coupled to the terahertz emitter 5 and to the terahertz receiver 6, and a suitably programmed evaluation unit. Differences to the previous embodiment example result only in the fact that here in each case only one terahertz emitter 5 and one terahertz receiver 6 are present in each case, and these are used for the first as well as for the second measurement. A pivotable holding device 17 for the container 1 is provided in each case, with which holding device the container 2 is fixed relative to the terahertz emitter 5 and to the terahertz receiver 6 and together with these can be rotated or tilted about an axis 18.

The respective arrangement is represented in each case twice next to one another in the FIGS. 2 and 3, and specifically on the left in a first position, in which the first measurement is carried out, and on the right in a second position, in which the second measurement is carried out. The location 8' of the wall 3, at which the second measurement is carried out, is here identical to the location 8, at which the first measurement is carried out, wherein there, with the first measurement, it is the gas 4 or the gas bubble containing the gas 4, and with the second measurement, it is the liquid 2 contacting the wall at an inner surface of the wall 3 which is to be determined.

Otherwise, the methods which are carried out with the arrangements from FIGS. 2 and 3, correspond to the previously described method with the single exception that the two measurements which here too are carried out for several frequencies, are necessarily carried out one after the other, since the holding device 17 must be pivoted between these measurements, in order to rotate or tilt the container 1.

Here, in any case absolutely identical measurement locations result for both measurements, by which means the first measurement becomes a perfect reference measurement. All typical disturbing or interfering effects on bottles, such as structuring, labels or contamination/dirt, then influence both measurements in exactly the same manner and thus can be easily and accurately eliminated, so that the accuracy of the method is not compromised.

The refractive index of the liquid 2 and thus the liquid 2 can be analysed very well with the suggested method amid the application of THz radiation, and specifically, as the case may be, despite its opacity to THz radiation. As a rule, the share of the THz radiation which is reflected at the respective boundary surface is detectable in a clear manner, since the container 1—in most cases a normal bottle—on the inside typically has a very smooth surface.

With a further development of the method described by way of FIGS. 2 and 3, the second measurement is carried out first of all and the container 1 is subsequently moved into a position which is suitable for the first measurement, whereupon several further measurements are carried out, which are successive in a defined temporal interval and with which the THz radiation is directed onto the same location 8 of the wall 1. Then a speed of a wetting change at the mentioned location 8 of the wall 1 can be determined from the measurement results of the further measurements.

The invention claimed is:

1. A method for determining a substance amid the application of THz radiation, with which a first and a second measurement are carried out, wherein the THz radiation is emitted in the direction of the substance for measuring characteristics of the substance, and a share of the THz radiation coming from the direction of the substance is detected, wherein the substance is a liquid and is located in a closed container which additionally contains a gas, wherein a wall of the container is transparent to THz radiation, wherein the THz radiation with the first measurement is directed onto a location of the wall, at which the gas or a bubble containing the gas contacts the wall, and the detected share of the THz radiation with the first measurement is reflected at a boundary surface between the wall and the gas or the bubble, whereas the THz radiation with the second measurement is directed onto a location of the wall, at which the liquid contacts the wall, and the detected share of the THz radiation with the second measurement is reflected at a boundary surface between the wall and the liquid, and wherein the first measurement serves as a reference measurement for a measurement result of the second measurement.

2. The method according to claim 1, wherein the location of the wall, onto which the THz radiation is directed with the second measurement, is identical to the location of the wall, onto which the THz radiation is directed with the first measurement, wherein the container is moved such that with the first measurement, the gas or the bubble, and with the second measurement, the liquid contacts the wall at this location.

3. The method according to claim 2, wherein the second measurement is carried out first and the container is subsequently moved into a position suitable for the first measurement, whereupon several further measurements are carried out, which are successive in a defined temporal interval, and with which the THz radiation is directed onto the same location of the wall, wherein a speed of the wetting change at the mentioned location of the wall is determined from the measurement results of the further measurements.

4. The method according to claim 1, wherein the container for the first and the second measurement is positioned in a lying manner and/or in a manner such that the gas collects in a region of the container, in which a vertical cross section of the wall of the container is circular and/or has a constant wall thickness.

5. The method according to claim 1, wherein a beam intensity of the share reflected at the boundary surface to the gas or to the bubble and which is measured with the first measurement is used as a reference value, and a refractive index of the liquid is determined in dependence on a ratio of a beam intensity of the share reflected at the boundary surface to the liquid and which is measured with the second measurement, and the reference value.

6. The method according to claim 5, wherein a refractive index of a material forming the wall is determined with the first measurement and/or the second measurement, and that the refractive index of the liquid is determined by way of a result of the second measurement being evaluated in dependence on the thus determined refractive index of the material forming the wall.

7. The method according to claim 1, wherein additionally to the mentioned share, a beam share reflected at an outer surface of the container is detected with the first measurement and/or with the second measurement, and that a travel time difference and/or intensity difference between the share reflected at the respective boundary surface between the wall and the gas or the liquid and the beam share reflected at the outer surface is determined.

8. The method according to claim 7, wherein an optical thickness of the wall is determined from the travel time difference and a measure for absorption behaviour of a material forming the wall is determined from the intensity difference.

9. The method according to claim 1, wherein the first and/or the second measurement in each case are carried out several times at different locations of the wall and/or at different frequencies of the THz radiation.

10. The method according to claim 1, wherein the first measurement and the second measurement in each case are carried out at different locations of the wall, wherein a picture is produced by way of a difference formation or ratio formation between results of the first and second measurement.

11. The method according to ene of the preceding claim 1, wherein it is carried out with a phase-sensitive THz system with at least one optically activatable THz transmitter antenna and at least one optically activatable THz receiver antenna for the coherent detection of the THz radiation produced by the THz emitter antenna, wherein the THz emitter antenna and the THz receiver antenna are activated by a common light source.

12. An arrangement for determining a liquid which is located in a closed container, comprising at least one terahertz emitter for producing THz radiation, at least one terahertz receiver for detecting the THz radiation, as well an evaluation unit connected to the at least one terahertz receiver, for evaluating output signals of the terahertz receiver, wherein the terahertz emitter and the terahertz receiver are arranged relative to one another such that the terahertz receiver is suitable for detecting the THz radiation produced by the terahertz emitter after a reflection at one or more defined locations of an inner surface of a wall of the container, and wherein the evaluation unit with regard to programming technology is configured to evaluate the output signals for a first measurement, with which a share of the THz radiation reflected at a boundary surface between the wall and a gas is detected, and for a second measurement, with which are share of the THz radiation reflected at a boundary surface between the wall and the liquid is detected and thereby to derive a reference value for an intensity of the detected THz radiation from the output signals for the first measurement and to evaluate the output signals for the second measurement in dependence on the reference value and by way of this to derive a refractive index of the liquid located in the container and/or to assign the liquid to a liquid class.

13. The arrangement according to claim 12, wherein it comprises a holding device for the container, for the terahertz emitter and for the terahertz receiver, in order to fix these relative to one another, wherein the container, the terahertz emitter and the terahertz receiver, by way of the holding device are commonly rotatable or pivotable between a first position for the first measurement and a second position for the second measurement such that a measurement point on the inner surface of the wall and which is identical for both measurements, in the first position is contacted by a gas located in the container additionally to the liquid or by a bubble containing this gas, and in the second position is covered by the liquid.

14. The arrangement according to claim 12, wherein it comprises two pairs in each case of a terahertz emitter and in each case a terahertz receiver, of which one is arranged higher than the other, wherein the higher arranged pair is provided for the first measurement on a gas located in the container additionally to the liquid, and the other pair for the second measurement on the liquid.

15. The arrangement according to claim 12, wherein the evaluation unit is configured, from the output signals, in each case to derive an intensity of a share reflected at an outer surface of the wall of the container and an intensity of a share of the THz radiation which is reflected at the inner surface of the wall of the container, as well as a travel time difference between these two shares.

16. The arrangement according to claim 15, wherein the evaluation unit is configured to derive an optical thickness of the wall of the container from the travel time difference, to derive a measure for an absorption behaviour of the wall material from the intensities of the share reflected on the outer surface of the wall and of the share reflected on the inner surface of the wall, in dependence on the optical thickness, to identify the wall material in dependence on this measure, as corresponding to a certain substance or belonging to a certain substance class, to determine the refractive index of the wall material, as corresponding to a value which is stored in a memory for this substance or for this substance class and to determine the refractive index of the liquid by way of evaluating a result of the second measurement in dependence on the thus determined refractive index of the wall material.

17. The arrangement according to claim 12, wherein the evaluation unit comprises a device for activating the terahertz emitter, which is configured to activate the terahertz emitter such that it produces the THz radiation successively or simultaneously at different frequencies, wherein the evaluation unit is configured to carry out at least one of the two measurements for each of these frequencies by way of evaluation of the output signals at the respective frequency.

18. The arrangement according to claim 12, wherein it comprises a conveying device for the automatic conveying of the container to a measurement location and/or for rotating or pivoting the container at the measurement location.

* * * * *